(12) United States Patent
Pierce et al.

(10) Patent No.: US 7,856,035 B2
(45) Date of Patent: Dec. 21, 2010

(54) METHOD AND APPARATUS FOR WIRELESS TRANSMISSION OF DATA

(75) Inventors: Mark R Pierce, Hoffman Estates, IL (US); Jason G Plackey, Arlington Heights, IL (US); William J Smirles, Deerfield, IL (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1394 days.

(21) Appl. No.: 10/881,013

(22) Filed: Jun. 30, 2004

(65) Prior Publication Data

US 2005/0249239 A1   Nov. 10, 2005

Related U.S. Application Data

(60) Provisional application No. 60/568,296, filed on May 5, 2004.

(51) Int. Cl.
H04J 3/24 (2006.01)

(52) U.S. Cl. ...................................... 370/473
(58) Field of Classification Search ....................... None
See application file for complete search history.

(56) References Cited

U.S. PATENT DOCUMENTS

| | | | |
|---|---|---|---|
| 5,319,363 A | 6/1994 | Welch et al. | |
| 5,678,562 A | 10/1997 | Sellers | |
| 6,093,146 A | 7/2000 | Filangeri | |
| 6,132,337 A | 10/2000 | Krupka et al. | |
| 6,160,478 A | 12/2000 | Jacobsen et al. | |
| 6,171,237 B1 | 1/2001 | Avitall et al. | |
| 6,302,844 B1 | 10/2001 | Walker et al. | |
| 6,364,834 B1 | 4/2002 | Reuss et al. | |
| 6,406,426 B1 | 6/2002 | Reuss et al. | |
| 6,443,890 B1 | 9/2002 | Schulze | |
| 6,485,416 B1 | 11/2002 | Platt | |
| 6,524,239 B1 | 2/2003 | Reed et al. | |
| 6,544,171 B2 | 4/2003 | Beetz et al. | |
| 6,544,173 B2 | 4/2003 | West et al. | |
| 6,544,174 B2 | 4/2003 | West et al. | |
| 6,558,320 B1 | 5/2003 | Causey, III et al. | |
| 6,564,104 B2 | 5/2003 | Nelson et al. | |
| 6,589,170 B1 | 7/2003 | Flach et al. | |
| 6,602,191 B2 | 8/2003 | Quy | |
| 6,616,606 B1 | 9/2003 | Petersen et al. | |
| 2001/0023315 A1 | 9/2001 | Flach et al. | |
| 2001/0029321 A1 | 10/2001 | Beetz et al. | |
| 2001/0034475 A1 | 10/2001 | Flach et al. | |
| 2001/0047125 A1 | 11/2001 | Quy | |
| 2002/0002326 A1 | 1/2002 | Causey, III et al. | |

(Continued)

OTHER PUBLICATIONS

"emWare's emLink™ Used to Internet-enable Welch Allyn's Vital Signs Monitor", dated Mar. 2, 1999.

*Primary Examiner*—Raj K Jain
(74) *Attorney, Agent, or Firm*—Burr & Brown (57) ABSTRACT

There are provided methods for selecting a communication protocol for formatting data and for wirelessly transmitting data, preferably medical data, e.g., electrocardiogram data, methods for reducing data and/or selecting from data, methods for adding data, methods for generating trend data, methods for rendering data, methods for inputting and/or transmitting addressee data and for transmitting data to the addressee (s) and/or notifying the addressee(s), and methods for wirelessly transmitting data to a server and transmitting data from the server, as well as systems for carrying out such methods.

23 Claims, 6 Drawing Sheets

U.S. PATENT DOCUMENTS

| | | |
|---|---|---|
| 2002/0013517 A1 | 1/2002 | West et al. |
| 2002/0013518 A1 | 1/2002 | West et al. |
| 2002/0046262 A1* | 4/2002 | Heilig et al. ............ 709/219 |
| 2002/0169584 A1 | 11/2002 | Fu et al. |
| 2002/0173704 A1 | 11/2002 | Schulze et al. |
| 2002/0198473 A1 | 12/2002 | Kumar et al. |
| 2003/0009088 A1 | 1/2003 | Korth et al. |
| 2003/0144579 A1 | 7/2003 | Buss |
| 2003/0171111 A1 | 9/2003 | Clark |
| 2003/0206116 A1 | 11/2003 | Weiner et al. |
| 2005/0021370 A1* | 1/2005 | Riff et al. ............ 705/2 |

* cited by examiner

METHOD AND APPARATUS FOR WIRELESS TRANSMISSION OF DATA

CROSS-REFERENCE TO RELATED APPLICATION

This application claims the benefit of U.S. Provisional Patent Application No. 60/568,296, filed May 5, 2004, the entirety of which is incorporated herein by reference.

FIELD OF THE INVENTION

The present invention relates to a method and apparatus for the wireless transmission of data. More particularly, the present invention relates to the wireless transmission of data via any of multiple methods, including the internet.

BACKGROUND OF THE INVENTION

There are a variety of fields in which rapid gathering and transfer of information is desirable or critical. In the field of emergency medicine, for example, the expeditious gathering and transfer of information regarding a patient's condition can have a primary effect on the outcome of an emergency situation. For example, without patient information prior to arrival at an emergency department, current national average door-to-dilation times are in the range of 104 minutes. In other words, a cardiac patient arriving at an emergency department may be delayed up to 104 minutes for dilation. This extended time can have a profound impact on patient health and survival rates.

Presently, several systems and methods exist for acquiring patient data and forwarding the data to qualified personnel at the emergency department prior to patient arrival. None of the current methods, however, are capable of transmission of patient vitals and/or transmission of electronic records with sufficiently rapid transmission times. For example, one current method of acquiring and transmitting patient data is to obtain patient data via an Electrocardiogram (ECG) device and perform transmission of the data by wireless facsimile (fax) via land lines or analog cellular telephones. However, these fax-based solutions can take in excess of two minutes to transmit the data. It is important in an emergency situation to provide comprehensive patient information to a receiving emergency department as quickly and as early as possible during a cardiac emergency, such as for the purpose of expediting the assembly of a catheterization lab team to reduce the aforementioned door-to-dilation time and minimize damage to heart muscle tissue caused by a heart attack.

A number of other devices and methods exist which relate to communicating medical information. For example, U.S. Pat. No. 6,602,191 is directed to a method and apparatus for a wireless health monitoring system for interactively monitoring a disease or health condition of a patient by connecting an internet-enabled wireless web device ("WWD") to a health monitoring device which may be a medical device or other health related device. The WWD may be connected to the health monitoring device directly by a wired connection to a generic input/output port of the WWD or wirelessly connected to the health monitoring device, such as via an infrared or radio frequency connection. The health related data is transmitted from the WWD to a server using standard internet protocols. The WWD can be a PDA equipped with a wireless modem.

U.S. Pat. No. 6,589,170 is directed to a medical telemetry system provided for collecting the real-time physiologic data of patients (including ambulatory patients) of a medical facility, and for transferring the data via RF signals to a real-time data distribution network for monitoring and display. The system includes battery-powered remote telemeters which attach to respective patients, and which collect and transmit (in data packets) the physiologic data of the patients. The remote telemeters communicate bi-directionally with a number of ceiling-mounted RF transceivers, referred to as "VCELLs," using a wireless TDMA protocol. The VCELLs, which are hardwire-connected to a LAN, forward the data packets received from the telemeters to patient monitoring stations on the LAN. The VCELLs are distributed throughout the medical facility such that different VCELLs provide coverage for different patient areas. As part of the wireless TDMA protocol, the remote telemeters continuously assess the quality of the RF links offered by different nearby VCELLs (by scanning the frequencies on which different VCELLs operate), and connect to those VCELLs which offer the best link conditions.

U.S. Pat. No. 6,485,416 discloses a physiological monitoring apparatus comprising a cellular phone handset connected to a cellular phone network. The handset includes a removable battery container (12) having a physiological monitoring device (14) contained therein as well as a battery power source (13). The battery pack container 12 has contained therein a battery power source 13 together with a bio-aquisition unit 14 which is preferably an ECG monitoring device which formulates the results of electrical cardiac activity detected by a bio sensor 15 which are preferably electrodes which are fixedly attached to the container 12.

U.S. Pat. No. 6,443,890 discloses a system and method for monitoring patient variables in a wireless mode via a patient worn monitoring device. The patient worn monitoring device connects to a variety of bio-sensors with at least one microphone for voice communications. The pertinent worn device connects to a wireless network and thence to the internet for transmitting voice and data to a health care provider. The health care provider communicates with the patient worn device via the internet and the wireless network to send instructions to the patient worn monitoring unit and to communicate via voice with the patent. According to the patent, among the data that can be transmitted is a digitally sampled electrocardiogram.

Despite existing technology, a need still exists for apparatus and methods which can acquire critical patient data and provide more rapid, reliable and/or accurate transmission of the data to a hospital or other emergency care facility to reduce overall transmission times and increase the patient's chances for survival.

SUMMARY OF THE INVENTION

It is an object of the present invention to overcome the problems of the prior art by providing a method and apparatus for the wireless transmission of data that is capable of rapid transmission time and can support the wireless transmission of electronic records.

In accordance with one aspect of the invention, there is provided a communication system, which includes means for receiving raw data, and means for automatically selecting a communication protocol from among a plurality of communication protocols, based on predetermined criteria for formatting and wirelessly transmitting data. The communication system in accordance with this aspect of the invention preferably further includes means for receiving the formatted data, means for rendering (i.e., converting data into a form which is more readily understandable by a human) the received data, means for transmitting the rendered data and means for receiving the transmitted rendered data.

In accordance with another aspect of the invention, there is provided a communication system which includes means for receiving raw data, means for communicating to a user at least one parameter to be used as a selection criterion and means for allowing the user to select a communication protocol from among a plurality of communication protocols for formatting and wirelessly transmitting data. The communication system in accordance with this aspect of the invention preferably further includes means for receiving the formatted data, means for rendering received data, means for transmitting the rendered data and means for receiving the transmitted rendered data.

In accordance with yet another aspect of the invention, there is provided a communication system, which includes an electrocardiogram-performing apparatus that generates raw data, and at least one of (1) means for automatically reducing the raw data by not less than 25% (e.g., about 75%); (2) means for rendering an image based on the raw data over a period of time; (3) means for permitting a user to select at least one segment of time from within the period of time based on the image; and (4) means for wirelessly transmitting a packet of data from the selected at least one segment of time to means for receiving the packet of data. The communication system in accordance with this aspect of the invention preferably further includes means for automatically selecting a communication protocol from among a plurality of communication protocols for wirelessly transmitting the data, and means for formatting the raw data from at least one segment of time according to the selected communication protocol to provide a packet of data prior to wireless transmission. Additionally, the communication system in accordance with this aspect of the invention preferably includes means for rendering the packet of data after wireless transmission, means for transmitting the rendered data, and means for receiving the transmitted rendered data.

In accordance with another aspect of the invention, there is provided a communication system, which includes means for wirelessly transmitting formatted data, means for receiving the formatted data, means for rendering the received data, means for transmitting the rendered data, and means for receiving the rendered data.

In accordance with still another aspect of the invention, there is provided a communication system, which includes means for acquiring raw data and supplying the raw data to means for receiving raw data, means for a user to input addressee data regarding at least one intended addressee, means for formatting the raw data, means for wirelessly transmitting the formatted data and the addressee data, means for receiving the formatted data and addressee data, means for receiving the formatted data and the addressee data, means for rendering the received formatted data and means for automatically transmitting the rendered data to the at least one intended addressee.

In accordance with yet another aspect of the invention there is provided a communication system, which includes means for acquiring raw data and means for supplying the raw data to means for receiving the raw data, means for formatting the raw data, means for wirelessly transmitting the formatted data, and means for receiving the formatted data, means for rendering received formatted data, means for transmitting the rendered data, means for receiving the rendered data, and means for automatically notifying a device associated with the means for receiving the rendered data.

In accordance with still another aspect of the invention there is provided a communication system, which includes means for acquiring raw data and supplying the raw data to means for receiving raw data, means for formatting the raw data, means for a user to input additional data, means for transmitting the formatted data and the additional data, means for receiving the formatted data and the additional data, means for rendering the received formatted data, means for transmitting the rendered data and the additional data, and means for receiving the formatted data and the additional data.

In accordance with yet another aspect of the invention, there is provided a communication system, which includes means for acquiring raw data and supplying the raw data to means for receiving raw data, means for a user to select a portion of the raw data, means for formatting the selected portion of the raw data, means for transmitting the formatted data, means for receiving the formatted data, means for rendering the received formatted data, means for transmitting the rendered data, and means for receiving the rendered data.

In accordance with another aspect of the invention, there is provided a communication system, which includes means for wirelessly transmitting data, a server for receiving the data, means for transmitting the data from the server, and at least one means for receiving the data from the server.

In accordance with another aspect of the present invention, there is provided a method of communicating, comprising: receiving raw data in a data-receiving device; automatically selecting from among a plurality of communication protocols a selected communication protocol; formatting the raw data according to the selected communication protocol; and transmitting the formatted data in the selected communication protocol.

In accordance with another aspect of the present invention, there is provided a method of communicating, comprising: receiving raw data in a data-receiving device; detecting at least one parameter (selected from the group consisting of: respective bandwidth detected to be available for each of a plurality of communication protocols, size of the raw data, communication methods available to the communication system, accuracy of data sent to a receiver and returned from the receiver in any one of the plurality of communication protocols, passage of time without data being received by a receiver, and quantity of dropouts after beginning to attempt to transmit data to a receiving device); communicating to a user the at least one parameter; selecting from among the plurality of communication protocols a selected communication protocol based on a selection by the user; formatting the raw data according to the selected communication protocol to provide formatted data; and wirelessly transmitting the formatted data in the selected communication protocol.

In accordance with another aspect of the present invention, there is provided a method of communicating, comprising: obtaining raw data; automatically reducing the raw data by not less than 25% (e.g., about 75%); rendering an image based on the raw data over a period of time; selecting at least one segment of time from within the period of time based on the image; and wirelessly transmitting a packet of data from the at least one segment of time to a data-receiving device.

In accordance with another aspect of the present invention, there is provided a method of communicating, comprising: wirelessly transmitting formatted data; receiving the formatted data in a data-receiving device; rendering the formatted data received by the data-receiving device to provide rendered data; transmitting the rendered data; and receiving the rendered data.

In accordance with another aspect of the present invention, there is provided a method of communicating, comprising: receiving raw data in a data-receiving device; inputting addressee data regarding at least one intended addressee selected by a user; formatting the raw data to provide formatted data; wirelessly transmitting the formatted data and the addressee data; receiving the formatted data and the addressee data in a receiving device; rendering data received by the receiving device to provide rendered data; and automatically transmitting the rendered data to the at least one intended addressee.

In accordance with another aspect of the present invention, there is provided a method of communicating, comprising: receiving formatted data; and rendering the formatted data to produce rendered data, the rendering being carried out in a way which minimizes the size of the rendered data.

In accordance with another aspect of the present invention, there is provided a method of communicating, comprising: acquiring raw data and supplying the raw data to a raw data-receiving device; formatting the raw data to provide formatted data; wirelessly transmitting the formatted data; receiving the formatted data in a receiving device; rendering data received by the receiving device to provide rendered data; transmitting the rendered data to at least one rendered data-receiving device; and automatically notifying a notification device respectively associated with each of the at least one rendered data-receiving device.

In accordance with another aspect of the present invention, there is provided a method of communicating, comprising: wirelessly transmitting data to a server; and transmitting the data from the server to at least one data-receiving device.

BRIEF DESCRIPTION OF THE DRAWINGS

For a full understanding of the nature and objects of the invention, reference should be made to the following detailed description of the invention, read in connection with the accompanying drawings in which.

DETAILED DESCRIPTION OF THE INVENTION

As previously mentioned, in one aspect of the present invention, a communication system is provided which includes means for receiving raw data and means for automatically selecting a communication protocol from among a plurality of communication protocols for formatting and wirelessly transmitting data. The communication protocol can be any protocol capable of transmitting electronic records rapidly enough to satisfy demands in the system. Representative examples of these types of protocols currently in use include MOBITEX®, cellular, and data radio.

In accordance with a preferred embodiment, the communication protocol is automatically chosen by the communication system based on one or more predetermined selection criterion. The one or more selection criterion may be selected from the group including, but not limited to: identifying which communication methods are available, the respective available bandwidth detected for each communication protocol, the detected accuracy of data sent to a receiver and returned from the receiver in any one of the communication protocols, the size of the raw data, the passage of time without data being received by a receiver, and the detected quantity of dropouts after beginning to attempt to transmit data to a receiving device.

Persons of skill in the art are readily familiar with a number of methods for identifying communication methods which are available, one such familiar method being referred to as "polling." Similarly, persons of skill in the art are readily familiar with methods for detecting bandwidth available for any particular communication protocol, one such method being to send one or more packets of data along with a command to return the data (or otherwise acknowledge having received the data), referred to as a "ping" test, and to then analyze the amount of data which was transmitted (and therefore which can be expected to be transmitted) in a given period of time. Likewise, accuracy of data sent to a receiver and returned from the receiver in any given communication protocol can be detected by any of a variety of well known methods, e.g., a ping test as described above. Also, persons of skill in the art are readily familiar with a variety of methods for detecting the size of a group of data. In addition, persons of skill in the art are readily familiar with methods for detecting elapsed time between sending a signal and receiving a signal back from a receiver and/or the receiver sending the entire group of data back to the transmitter for comparison. Similarly, persons of skill in the art are readily familiar with methods for detecting the number of times that a "dropout" (i.e., loss of communication) occurs while attempting to transmit data to a receiving device. All of the various methods for achieving the different functions described above in this paragraph are within the scope of the present invention.

For example, an embodiment which accomplishes the above-described automatic protocol selection can carry out any of the methods described above, or combinations thereof, e.g., eliminating from consideration at a particular time any communication methods which, when tested, do not return accurate data, testing each of the available communication methods to determine the available bandwidth for each communication protocol, and then initially selecting the available accurate communication method which provides the greatest bandwidth. Based on that selection, the data to be transmitted can then be formatted for transmission via such protocol. If at some point it is determined that the data is not successfully being transmitted via that communication protocol, the system can then change its selection of communication protocol to the available accurate communication method which was found to have the next largest available bandwidth, then format the data according to that protocol, and then proceed with attempting to transmit the data via that protocol. Accordingly, according to the present invention, it is possible to select a transmission mechanism based on one or more criterion selected from among transmission speed, packet error rate, delay times and other characteristics, in order to minimize transmission time and maximize data integrity.

Alternatively, the communication system has a programmed sequence among the communication protocols, such that the communication system automatically shifts to a next most favorable communication protocol after a failure to communicate is identified using a currently selected communication protocol and/or where selection criteria described above indicate that a particular communication protocol is not expected to be effective (e.g., in terms of accuracy of data received, frequency of dropouts, etc.). A communication failure can be determined by examining passage of time without data being received by a receiver or a detected quantity of dropouts after beginning to attempt to transmit data to a receiving device. Preferably, a user can override the programmed sequence, if desired.

The communication system in accordance with this aspect of the invention preferably further includes means for acquiring raw data and supplying the raw data to the means for receiving raw data. In a preferred embodiment, the means for acquiring raw data is a device for performing an electrocardiogram.

Preferably, the communication system according to this aspect of the invention further includes means for generating patient trend data based on the raw data. The raw data and trend data are preferably formatted in accordance with the selected communication protocol to provide formatted data conducive to the selected transmission method. Persons of skill in the art are readily familiar with formatting data to be conducive to transmission using known communication protocols.

The communication system in accordance with this aspect of the invention preferably further includes means for transmitting the formatted data, means for receiving the formatted data, means for rendering the received formatted data, means for transmitting the rendered data, and means for receiving the rendered data.

The expression "rendered" and the expression "rendering" as used herein refer to converting data into a form which is more readily understandable by a human, e.g., taking raw data such as data obtained by an electrocardiogram-performing device and converting the data into a graphical format, e.g., a plot in the form of a PDF image. There are an extremely wide range of techniques by which data can be converted into forms which are more readily understandable, and all such techniques are included in the various aspects of the present invention as described herein.

In accordance with another aspect of the invention, a communication system is provided which includes means for communicating at least one parameter to a user to allow the user to select a communication protocol from among the plurality of communication protocols available for formatting and then wirelessly transmitting the raw data. The aforementioned parameter can be selected from among the same group used to automatically select the communication method as previously described.

In accordance with this aspect of the present invention, the system may have the option of locking out the user from selecting a communication protocol for an initial period of time, e.g., two minutes, during which the user cannot interfere with the automatic selection of a communication protocol by the system (after such initial period, the user would be able to, if desired, select a communication protocol for wireless transmission of the data).

In accordance with another aspect of the present invention, a communication system is provided which includes means for rendering an image based on the raw data over a period of time and means for permitting a user to select at least one segment of time from within the displayed period of time based on the image. The electrocardiogram-performing device preferably further reduces the raw data by not less than 25% (e.g., about 75%), which provides for improved transmit times and allows data covering a larger time span to be transmitted. The reduced data is then formatted and transmitted in accordance with the selected protocol as previously described.

In accordance with another aspect of the present invention, there is provided a communication system which includes means for wirelessly transmitting formatted data, means for receiving the formatted data, means for rendering the received data, means for transmitting the rendered data, and at least one means for receiving the rendered data.

In accordance with additional aspects of the present invention, there are provided communication systems which include means for a user to input additional data (e.g., patient data) and/or means for a user to input addressee data. The patient data can be patient information such as the patient's name, age, weight, current medication and/or vital signs, and/or user comments regarding patient condition. The patient data and/or addressee data are preferably wirelessly transmitted along with the formatted data. The addressee data is used to cause the system to automatically forward the rendered data to the intended addressee(s). Additionally, the addressee data can be used to perform automatic notification, for example, paging to alert intended addressee(s) to incoming data.

In accordance with another aspect of the present invention, there is provided a communication system which includes means for rendering data in a way which minimizes the size of the data, e.g., by defining geographically a series of points instead of identifying each point. One representative example, for instance, is to define line segments which approximate a plurality of data points, instead of identifying each data point which is approximated by that line segment.

In accordance with another aspect of the present invention, there is provided a communication system which includes means for acquiring raw data and supplying it to means for receiving the raw data, means for formatting the raw data, means for wirelessly transmitting the formatted data, means for receiving the formatted data, means for rendering the received data, means for transmitting the rendered data, at least one means for receiving the rendered data, and means for automatically notifying a notification device, e.g., a paging device, respectively associated with each of the at least one means for receiving the rendered data. Optionally, the communication system includes means for automatically retrying a notification when a notification is not confirmed as having been received; preferably, the communication system automatically retries such a notification a set number of times; preferably, the communication system automatically retries a default number of times, and the user can, if desired, select a number of retries which differs from the default. In additional, the communication system optionally further includes means to allow a user to select between automatic notification on arrival of every data transmission and automatic notification only on arrival of data for a new patient.

In accordance with an option according to the present invention, the user can select one or more segments of data which provide the best information to a receiver. For example, where the data is to be used in providing a visual representation, the user would be able to select a segment of data which provided the best visual view of data for showing the subject matter under observation, e.g., a patient being treated.

The means for transmitting the formatted data preferably includes at least one modem, for example, which is capable of executing at least one of the communication protocols detailed above. The means for receiving the formatted data can be any device capable of receiving and processing the formatted data.

Preferably, the means for wirelessly transmitting formatted data retains data only for the duration of a single transmission (i.e., once it receives confirmation that a group of formatted data was accurately and completely received by the means for receiving formatted data, that group of data is deleted from the memory of the means for wirelessly transmitting formatted data), such that there is never a risk of referencing "old" data.

In order to receive data which can be transmitted by any of the available communication protocols, the means for receiving the formatted data should be capable of accepting data in any of the formats of any of the communication protocols which can be used to wirelessly transmit the data.

Typical devices for receiving formatted data include personal computers and servers, for example. The means for receiving the rendered data can be any device capable of receiving and displaying the rendered data as a hard copy, such as a printer, or on a viewable screen such as are associated with personal computers, servers, cellular telephones, pagers and personal digital assistants, for example.

By comparison to the communication systems and methods according to the present invention, in facsimile-based devices, data is typically transmitted as a graphical image, as opposed to an electronic record, and therefore, further manipulation of the data is not as readily achievable. In addition, in order for data to be transmitted through facsimile-based devices, the data has to be in the format of a graphical image, which increases the size of the data and which therefore tends to cause transmission to take a longer period of time.

In general, current facsimile-based devices connect an onboard facsimile modem to a standard phone line or Cellular phone to transfer data to a facsimile machine. While faxing is a widely accepted practice, it has a number of disadvantages, including the following:

transmission times can be on the order of several minutes;

a facsimile transmission transfers a graphical image, not an electronic record—electronic records can readily be imported into an EMR database;

facsimile image quality is limited;

local phone service is not always available at the point of patient care; and cellular phone service with faxing capabilities tend to be limited in availability.

Future customer requirements for emergency care of patients outside the hospital environment will no doubt require the wireless delivery of more patient information, faster delivery times, and EMR importing/exporting capabilities into other systems. Implementing wireless transfer of electronic records would be of great importance in helping to save lives and improve care. The inherent flexibility of electronic records would significantly enhance efficiency, accuracy, and quality of care.

In accordance with another option in accordance with the present invention, the user can be given the capability of choosing the amount of data to be sent based on information as to the amount of bandwidth available (e.g., if a large amount of bandwidth is available, the user can request that all of the available data be sent, instead of allowing the system to automatically reduce the quantity of data being transmitted).

In accordance with another option in accordance with the present invention, the communication system may include an event log, e.g., in the means for wirelessly transmitting formatted data, in the means for receiving formatted data, in the means for transmitting rendered data and/or in the means for receiving rendered data. Examples of data which can optionally be logged into such an event log(s) include:

a successful wireless transmission to the means for receiving formatted data;

an unsuccessful wireless transmission to the means for receiving formatted data (in addition, an alarm indication, e.g., Single Tone, 600 msec, 500 Hz., may also be given);

a successful transfer to a means for receiving rendered data (such as a PDA); and an unsuccessful transfer to a means for receiving rendered data (in addition, an alarm indication, e.g., Single Tone, 600 msec, 500 Hz., may also be given).

Accordingly, the present invention provides systems and methods by which data can be sent wirelessly from any of a wide variety of locations, e.g., a remote device (for example, a portable intensive care device including an electrocardiogram-performing device located at a shopping mall, in an airplane which is stationary or in transit, etc.), an ambulance (which stationary or in transit), a helicopter (which is stationary or in transit), etc., any of which may or may not have one or more permanent modem or other data transmitting device.

Figure 1:
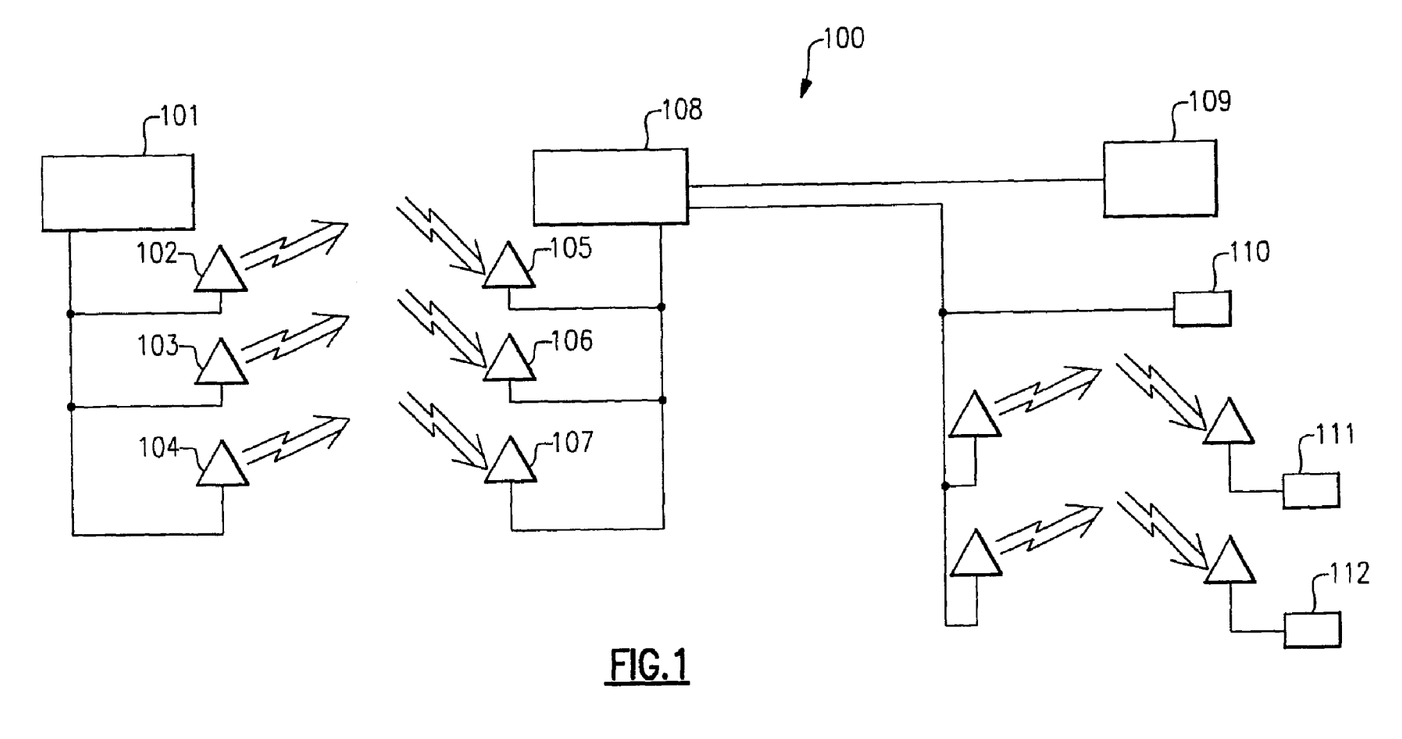
FIG. 1 is a schematic block diagram of a wireless data transmission system in accordance with one embodiment of the present invention.

FIG. 1 is a functional block diagram of an embodiment of a wireless data transmission system 100 in accordance with the present invention. In the depicted embodiment, data acquisition device 101 collects and formats data according to the appropriate wireless transmission method as will be discussed below in more detail. Data acquisition device 101 is coupled to multiple wireless transmission devices 102, 103, 104 that perform various types of wireless data transmission. The wirelessly transmitted data is received through the corresponding wireless data receiver 105, 106, 107, which are coupled to destination server 108. Destination server 108 is a user configurable device that performs pre-specified actions in accordance with user-selected parameters. For example, destination server 108 can provide a hard copy printout of the data via printer 109, e-mail the data to a personal computer 110 or PDA 111, or perform automatic paging via pager 112.

Figure 2:
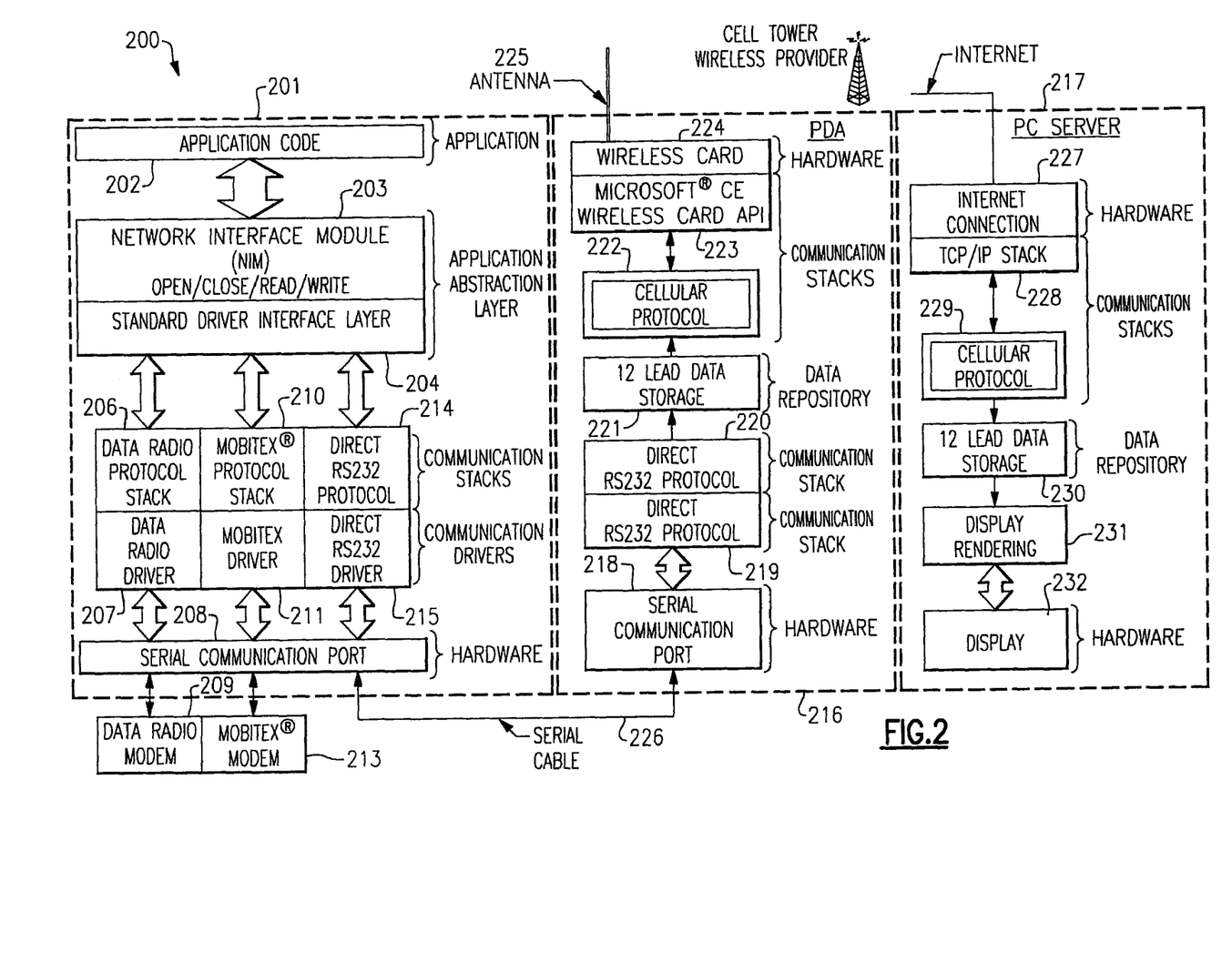
FIG. 2 is a schematic block diagram showing the hardware and software modules of a wireless data transmission system in accordance with one embodiment of the present invention.

FIG. 2 is a schematic block diagram showing the hardware and software modules of a wireless data transmission system in accordance with one embodiment of the present invention. Referring to FIG. 2, data acquisition device 201 is a programmable device that collects data in accordance with application code software module 202 and forwards the data to network interface software module 203 and standard driver interface layer software module 204, which together comprise application abstraction layer 205. Application abstraction layer 205 formats the collected data and appends a destination location record which includes, but is not limited to, a destination name, phone number, IP address, etc. as required by the selected wireless communication method. In accordance with one aspect of the present invention, data acquisition device 201 automatically selects the wireless communication method. In accordance with another aspect of the present invention, the user can manually select the wireless communication method. The formatted data is forwarded to the appropriate wireless data transmission path in accordance with the selected wireless transmission method.

The present invention establishes a robust set of communication protocols, based on the type of data transmission that is going to occur, to handle bad data, dropouts, cell switching, data packet validity and host verification. Three different types of data transmission are shown in the embodiment depicted in FIG. 2. The data radio transmission includes the data radio protocol stack software module 206, data radio driver software module 207, serial communications port 208 and data radio modem 209. The MOBITEX® transmission includes the MOBITEX® protocol stack software module 210, MOBITEX® driver software module 211, serial communications port 208 and MOBITEX® modem 213. The wireless internet transmission includes direct RS232 Protocol software module 214, direct RS232 driver software module 215, serial communications port 208 and portable wireless internet device 216. Portable wireless internet communications device 216 can be any device capable of receiving formatted data via an RS232 cable as well as performing wireless internet communications.

In the embodiment shown in FIG. 2, portable wireless internet communications device 216 is a Personal Digital Assistant (PDA). However, portable wireless communication device 216 can instead be a tablet PC, cell phone or any device capable of performing the previously defined communications.

In accordance with the selected communication path, the selected communication protocol forwards the formatted data to the corresponding communication driver, which sends the formatted data to the corresponding wireless communication device 209, 213, 216 through serial communication port 208. The wireless communication device 209, 213, 216 wirelessly transmits the data, which is subsequently received by destination server 217.

In accordance with the present embodiment, the portable wireless communication device 216 is a PDA that includes serial communication port 218 for receiving the formatted data from data acquisition device 201, direct RS232 driver software module 219, direct RS232 protocol software module 220, data repository 221, cellular protocol 222, wireless card application program interface (API) 223, wireless card 224 and antenna 225.

Direct RS232 driver 219 and direct RS232 protocol 220 are software modules that receive the formatted data from the serial communication port 208 via cable 226 and temporarily store the formatted data in data repository 221 prior to wireless transmission. While the formatted data is stored in data repository 221, the user can append pertinent information through a keyboard connected to, or integrated with, portable wireless internet communication device 216. Cellular protocol software module 222 then opens a socket connection, as is known in the art, to the IP address contained within the destination location record that was appended to the formatted data as previously discussed. The formatted data and appended information, if any, is next formatted by cellular protocol software module 222 and wireless card API software module 223 such that it can be wirelessly transmitted via any wireless service provider such as AT&T, Sprint, Cingular, etc., and is not carrier dependent. Wireless card 224 then wirelessly transmits the formatted data through antenna 225 via the aforementioned socket connection to destination server 217 at the IP address contained within the destination location record. Cellular protocol software module 222 is a robust protocol that is capable of reliably recovering from a loss of cellular signal and/or dropped data packets.

Destination server 217 includes internet connection 227, TCP/IP (Transmission Control Protocol/Internet Protocol) stack 228, cellular protocol 229, data repository 230, display rendering software module 231 and display 232.

Destination server 217 receives the formatted data via internet connection 227 and TCP/IP stack 228 and cellular protocol software module 229. The cellular protocol software module 229 extracts the originally acquired data, which is placed in data repository 230. Destination server 217 then performs actions requested by the user. For example, destination server 217 can be configured to render the received data in a readable format and provide a visual representation of the data via display 232 or a hardcopy printout via a printer (not shown). Destination server 217 may further be configured to notify appropriate personnel of the received data via e-mail, telephone and/or paging functions. Additionally, the rendered data may be forwarded to appropriate personnel for viewing on a separate computer monitor or PDA.

In accordance with a preferred embodiment, the wireless data transmission system acquires patient electrocardiogram (ECG) data and other vital information for wireless transmission to a destination server located at a hospital or other facility where qualified emergency service personnel are notified.

Figure 3:
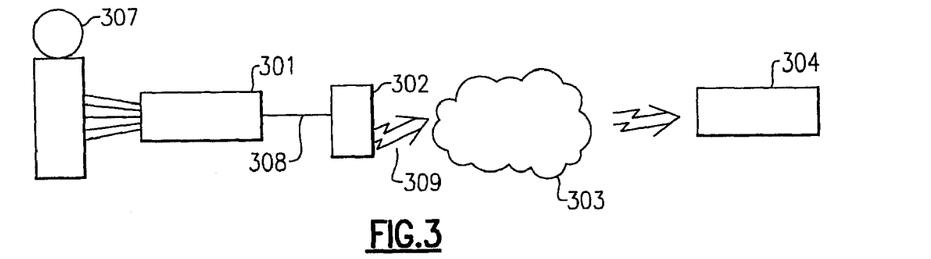
FIG. 3 is a schematic block diagram of a wireless data transmission system in accordance with a preferred embodiment of the present invention.

FIG. 3 is a schematic block diagram of a wireless data transmission system in accordance with a preferred embodiment of the present invention. In accordance with the embodiment depicted in FIG. 3, the data acquisition device comprises an electrocardiogram-performing device 301 connected to a patient 307 for acquisition of ECG data. Electrocardiogram-performing device 301 collects ECG and other patient data and formats the data in accordance with the transmission method to be used as will be discussed below in more detail. The formatted data is transferred from the electrocardiogram-performing device 301 to the portable transmission device 302 via cable 308 serially connected between the electrocardiogram-performing device 301 and the portable transmission device 302. The portable transmission device 302 performs wireless transmission of the formatted data 309 through the wireless medium 303 in accordance with the selected transmission method as will be discussed in more detail below. Destination server 304 receives the formatted data where it is stored in a file. Depending on the preselected parameters, destination server 304 then renders the data in a viewable format and performs notification of emergency service personnel as appropriate.

In an example of an electrocardiogram process using a wireless data transmission system according to the embodiment depicted in FIG. 3, ten leads are connected from the electrocardiogram-performing device 301 to the patient 307 to collected eight vectors (leads I, II, V1, V2, V3, V4, V5 and V6) and ten seconds of patient ECG waveform raw data is captured by the electrocardiogram-performing device 301 for each of the ten leads, as is known in the art. ECG data is typically acquired at a diagnostic quality rate of 500 samples per second, for example. The ECG waveform raw data is stored in flash memory in the electrocardiogram-performing device 301 as Leads I, II, V1, V2, V3, V4, V5, V6. When the ECG waveform raw data is retrieved from flash memory, lead III, aVR, aVL, and aVF are derived from the existing lead information providing a total of twelve leads of information.

The electrocardiogram-performing device 301 stores each sample internally as a 16-bit WORD. Each ECG snapshot has two associated identifiers, a patient ID and a snapshot ID. The electrocardiogram-performing device 301 generates both the patient ID and snapshot ID automatically prior to data acquisition. Two or more ECG snapshots may have the same patient ID if acquired within the context of the same incident. No two snapshots, however, may have the same snapshot ID.

After the ECG snapshot has been acquired and stored by the electrocardiogram-performing device 301, the operator can use electrocardiogram-performing device 301 to perform analysis on the acquired ECG waveform data. The analysis option appears within the acquisition menu of the electrocardiogram-performing device 301. If analysis is performed, the results are stored as part of the ECG snapshot record.

The electrocardiogram-performing device 301 preferably also provides a feature called trending. The electrocardiogram-performing device 301 can be configured to record all of the patient vital signs parameters available (such as blood pressure, heart rate, temperature, $SpO_2$, $CO_2$, IBP, NIPB, $ETCO_2$, respiratory rate, 12-lead data, and optional single lead ECG snapshot) on a configurable time periodic basis. If trending is enabled on the electrocardiogram-performing device 301, preferably the most recent data, e.g., the most recent 30 minutes of trend data available for a given patient, will be stored as part of an acquired ECG snapshot record. One example of a suitable electrocardiogram-performing device 301 is Model Number 971083E sold by Welch Allyn of Skaneateles Falls, N.Y.

After an ECG snapshot has been acquired (along with all associated data, such as analysis results and trend data), the wireless communication method is selected either automatically by the electrocardiogram-performing device 301 or manually by the operator. The wireless communication methods can be selected from the group including, but not limited to, data radio, MOBITEX®, and internet. The present embodiment will be explained using the internet as the wireless communication method. However, those skilled in the art will appreciate that the wireless data transmission system can perform other wireless transmissions such as data radio and MOBITEX®, and the invention is not thereby limited.

The user next connects electrocardiogram-performing device 301 to portable wireless transmission device 302 via serial cable 308 and powers on portable transmission device 302. As previously discussed, direct RS232 protocol 210 and direct RS232 driver 209 as shown in FIG. 2 download patient data serially from the electrocardiogram-performing device 301.

In a preferred aspect of the present invention, once electrocardiogram-performing device 301 has been connected to portable transmission device 302 via serial cable 308, the operator navigates to the transmission medium menu on the electrocardiogram-performing device 301. In an alternate embodiment, the electrocardiogram-performing device 301 automatically detects the transmission medium supported by the connected portable transmission device. In a preferred aspect of the present invention, the transmission medium is a wireless cellular data network. As previously discussed, the wireless data transmission system of the present invention supports transmission of patient vital information and electronic records with fast transmission times. For example, electronic records are typically transferred in a time span on the order of a few seconds, as opposed to minutes as in current faxed based systems.

Using the menu buttons on the electrocardiogram-performing device 301, the operator selects the desired destination location from the destination list. Upon selecting a destination, the electrocardiogram-performing device 301 downsamples and compresses the ECG waveform data for the selected ECG snapshot prior to serially transmitting to the portable transmission device 302.

The ECG waveform data for the selected ECG snapshot is first downsampled from its original sampling rate of 500 samples per second to minimize the amount of data being sent wirelessly by the portable transmission device 302. Preferably, the sampling rate is configurable on the electrocardiogram-performing device 301 to downsample the ECG snapshot from 500 samples per second to 375, 250, 170, or 125 samples per second, for example. Preferably, by default, the ECG waveform data is downsampled, e.g., from 500 to 125 samples per second. The downsampling function can be capable of being disabled on the electrocardiogram-performing device 301, if desired.

Figure 4:
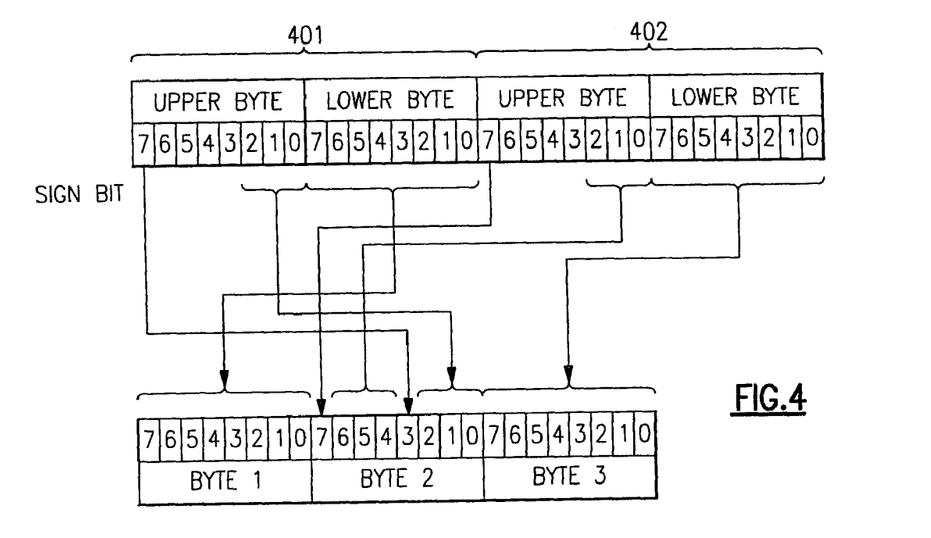
FIG. 4 is a schematic representation of an example of a data compression process in accordance with an embodiment of the present invention.

The ECG waveform data is then compressed by the electrocardiogram-performing device 301 using a nibble packing process as will now be described in more detail. As previously discussed a 12-bit ECG snapshot is stored as a 16-bit WORD. FIG. 4 is a schematic representation of an example of a data compression process in accordance with an embodiment of the present invention. As shown in FIG. 4, two 12-bit ECG data samples 401, 402 occupy 32 bits of memory within electrocardiogram-performing device 301. Prior to transmission, two 12-bit samples 401, 402 are converted into 24 bits of contiguous memory, compressing the ECG waveform data by an additional 25%.

For example, the lower byte of 12-bit sample 401 is stored in the first 8 bits (byte 1) and the lower byte of 12-bit sample 402 is stored in the last 8 bits (byte 3) of the 24 bits of contiguous memory. The upper byte of 12-bit sample 401 and the upper byte of 12-bit sample 402 are both stored in the middle 8 bits (byte 2) of the 24 bits of contiguous memory.

Figure 5:
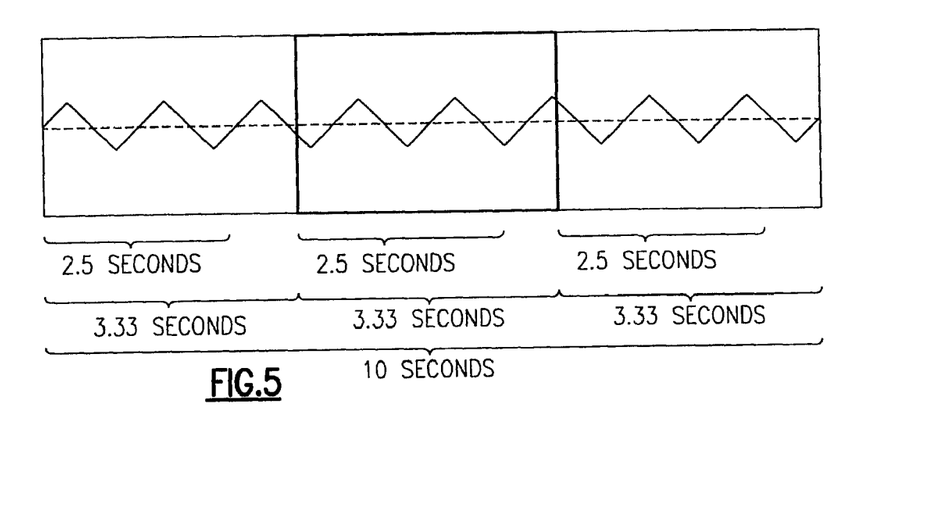
FIG. 5 is a graphical representation of an ECG snapshot broken into three equal 3.33 second time frames.

Because ECG snapshots are displayed on recipient devices in an industry-standard 4×3 format, electrocardiogram-performing device 301 preferably does not send all ten seconds of each of the 12 leads during a transmission. Instead, electrocardiogram-performing device 301 preferably provides the operator with the ability to select from one of three 3.33-second segments to transmit as shown in FIG. 5.

In a preferred aspect of the present invention, the electrocardiogram-performing device 301 always transmits the complete ten seconds of lead II, and for the remaining 11 leads transmits only the first 2.5 seconds of the selected 3.33-second segment.

The following are two specific examples of representative data transfer specifications:

1. MOBITEX® 12-Lead Data Transmission

MOBITEX® 12-Lead transmission shall support the following data format:

125 samples per second 2.5 seconds of data for leads: I, III, aVr, aVL, aVF, V1, V2, V3, V4, V5, V6.

10 seconds of data for lead II.

2.384 µVolts per bit, 12 bit range.

Filter Ranges with Rev M 12-Lead preamp software

Filtered response diagnostic 0.25 to 50

Response diagnostic 0.05 to 150

2. Wireless 12-Lead Data Transmission

The Wireless 12-Lead transmission shall support the following data format:

125 (Optionally 375, and 500) samples per second 2.5 (Optionally 3.3) seconds of data for leads: I, III, aVr, aVL, aVF, V1, V2, V3, V4, V5, V6.

10 seconds of data for lead II.

2.384 µVolts per bit, 12 bit range.

Filter Ranges with Rev M 12-Lead preamp software

Filtered response diagnostic 0.25 to 50

Response diagnostic 0.05 to 150

As discussed above, preferably, the user has the option of adjusting the amount of data to be sent based on the detected quantity of available bandwidth. For example, where the system determines that a very large amount of bandwidth is available, the user might have the option of specifying that the system not downsample at all, and instead send the entire 10 seconds of data from each of the twelve leads.

Also, as mentioned above, preferably, the user has the option of selecting a segment of data which provides the best visual view of the data. For example, if the user detects that a particular segment of time produced data which provides a visual view which reflects accurately the patient's condition, the user would have the option of selecting that specific data for transmission.

Prior to serial transmission, the patient name field associated with the ECG snapshot is preferably encrypted, e.g., 40-bit RSA encrypted, by the electrocardiogram-performing device 301, as is known in the art for patient confidentiality and security purposes.

Once the ECG waveform data has been downsampled and compressed, the electrocardiogram-performing device 301 establishes a serial connection with portable transmission device 302 and begins data transmission.

Referring again to FIG. 3, portable transmission device 302 includes a wireless modem 309 either externally connected or internally integrated. Wireless modem 309 provides the internet connection used to transmit data from portable transmission device 302 to destination server 304. Examples of devices which can be used as the portable transmission device 302 include Windows CE and Pocket PC based devices, such as an iPaq, an Axim, a Pocket PC Phone or a tablet P.C., for example.

In a preferred aspect according to the embodiment shown in FIG. 3, when the software is initiated on portable transmission device 302, a serial connection is opened, and electrocardiogram-performing device 301 begins data transmission. Both the serial port and the baud rate are user configurable from within the software resident on portable transmission device 302. Once portable transmission device 302 receives the complete ECG snapshot transmission, electrocardiogram-performing device 301 closes its serial channel and has no further role in the transmission process.

The software on portable transmission device 302 analyzes the ECG snapshot data to read the destination location. The destination location data (i.e., the server name and IP address) is appended to the ECG snapshot prior to serial transmission from electrocardiogram-performing device 301 to portable transmission device 302 as previously discussed. Using the software resident on portable transmission device 302, the operator can optionally enter a patient's demographics, vital statistics, or other related information. The information entered via portable transmission device 302 is appended to the ECG snapshot in memory.

Portable transmission device 302 then opens a socket connection to the IP address contained within the destination location record of the ECG snapshot as is known in the art. In the present embodiment, portable transmission device 302 uses a socket-based communication protocol that resides on top of TCP/IP, to communicate with destination server 304 to transmit the ECG snapshot data. The internet communication protocol used to transmit data from portable transmission device 302 to destination server 304 is bi-directional and mandates a positive response from destination server 304. The communication session between portable transmission device 302 and destination server 304 continues until either portable transmission device 302 receives a positive confirmation from destination server 304 that a complete ECG snapshot has been successfully received, the portable transmission device operator explicitly aborts the transmission, or portable transmission device 302 encounters an unrecoverable socket error (such as an invalid destination IP address entered on the electrocardiogram-performing device 301) and cannot continue.

Once destination server 304 has successfully received a complete ECG snapshot transmission, a positive delivery confirmation is sent to portable transmission device 302. If portable transmission device 302 does not receive a positive delivery confirmation from destination server 304, portable transmission device 302 polls destination server 304 until either a positive delivery confirmation is received, a negative delivery confirmation is received or portable transmission device 302 determines that communication with destination server 304 has terminated. When a negative delivery confirmation is received, or portable transmission device 302 determines that communication with destination server 304 has terminated, portable transmission device 302 attempts to open a new socket connection to the IP address contained within the destination location record of the ECG snapshot to retransmit the data. When a positive delivery confirmation is received, portable transmission device 302 closes its socket connection and returns to an idle state, waiting for another serial transmission from electrocardiogram-performing device 301.

Figure 6:
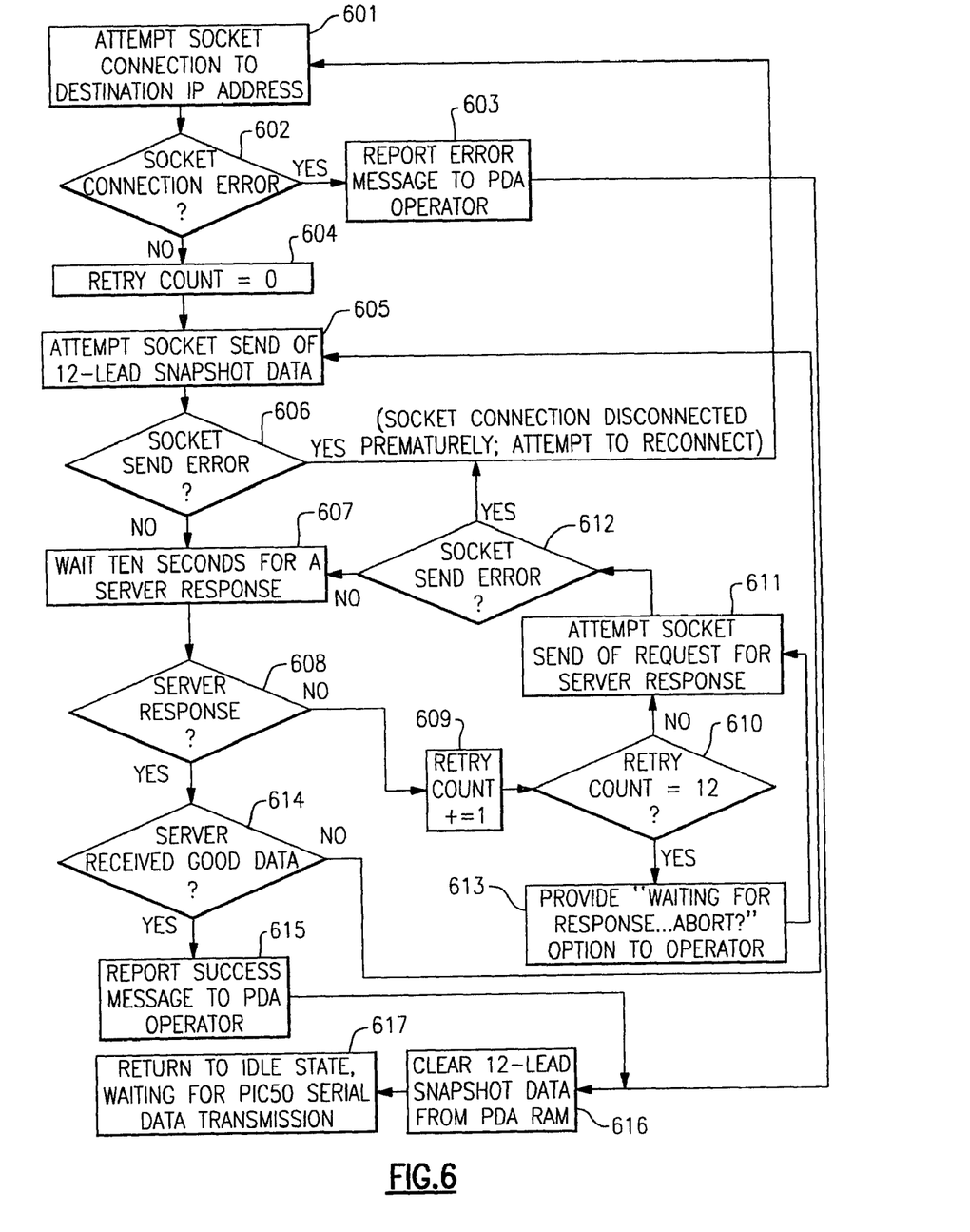
FIG. 6 is a flow chart detailing a wireless internet communication protocol in accordance with an embodiment of the present invention.

FIG. 6 is a flow chart detailing a wireless internet communication protocol in accordance with an embodiment of the present invention. Referring to FIG. 6, the protocol resident on portable transmission device 302 starts by opening a socket connection to the destination IP address in step 601. If a socket connection error occurs in step 602, the error is reported to the portable transmission device operator in step 603, the ECG snapshot data is cleared from the portable transmission device memory in step 616 and portable transmission device 302 returns to an idle state waiting to receive another serial transmission from electrocardiogram-performing device 301. If the socket connection successfully opens in step 602, portable transmission device 302 initializes the retry count to zero in step 604. The retry count will be explained later in more detail. Following a successful socket connection, portable transmission device 302 attempts to send the ECG snapshot data in step 605. If a socket send error occurs as shown in step 606, portable transmission device 302 attempts to reopen a socket connection as shown in step 601 and the process repeats as previously described. If a socket send error does not occur, portable transmission device 302 waits for ten seconds for a response from destination server 304 as shown in step 607. If a response is not received from destination server 304 in step 608, the protocol increments the retry count in step 609. The protocol then determines in step 610 if the retry count has reached 12, indicating 12 attempts to secure a response from destination server 304. If the retry count has reached 12, the protocol provides a "waiting for response . . . abort?" option as shown in step 613 to the portable transmission device operator. If the retry count has not reached 12, then in step 611, the protocol attempts a socket send of request for server response. If a socket error then occurs in step 612, the protocol again attempts to open a socket connection to the destination IP address and the process continues as previously described. If a socket error does not occur in step 612, the protocol returns to step 607 and waits for ten seconds for a response from destination server 304 as previously described.

If a server response is received in step 608 and the server response indicates good data as shown in step 614, the protocol reports a success message to the portable transmission device operator in step 615, clears the ECG snapshot data from the portable transmission device memory in step 616 and returns to an idle state waiting for electrocardiogram-performing device 301 to send new serial data in step 617. If the server response in step 614 does not indicate that destination server 304 received good data, then the protocol attempts to again send the ECG snapshot data as shown in step 605 and the process repeats as previously described.

Figure 7:
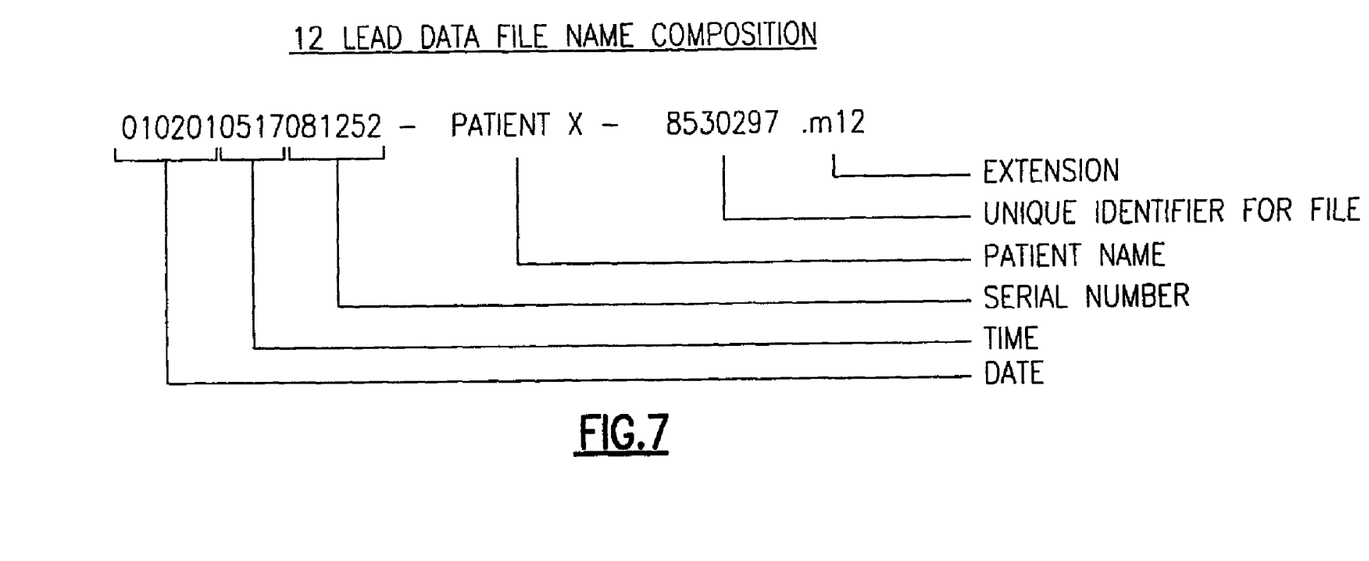
FIG. 7 is an example of a file naming convention in accordance with an embodiment of the present invention.

In a preferred aspect of the embodiment depicted in FIG. 3, destination server 304 is a Windows 2000 or Windows XP based PC machine. After receiving a complete ECG snapshot transmission, and sending a positive delivery confirmation to portable transmission device 302, destination server 304 saves the newly received ECG transmission to a persistent file. The filename used to identify a given ECG snapshot is preferably generated using the patient's name, the serial number of electrocardiogram-performing device 301 on which the ECG snapshot was acquired, the current date and time, as well as a unique identifier derived from the destination server's internal clock. The unique identifier is used to handle cases in which the same ECG snapshot is sent multiple times. FIG. 7 illustrates one example of a naming convention applied to received ECG snapshot files.

Once the ECG snapshot has been saved, destination server 304 opens the data file and reads its contents. The destination server 304 software provides several user-configurable automated functions that can be performed upon receiving an ECG snapshot transmission. These automated functions include, but are not limited to, automatically opening the ECG snapshot and displaying its contents on destination server 304; automatically printing a hardcopy of the ECG snapshot data to a configured printer; automatically sounding a configurable audible tone such as a wave file on a configurable time interval; automatically rendering the patient information as a PDF or other type of graphic type format file; automatically e-mailing the rendered information to one or more configurable recipients; and automatically dialing one or more numeric pager numbers via an installed modem. The destination server 304 software provides several options used to configure these automated functions which will now be described in more detail.

When the auto open option is enabled, a received ECG snapshot transmission will be opened and the snapshot data will automatically be displayed on the destination server's screen. The ECG snapshot data is displayed in the 4×3 format described earlier. Analysis results and trend data are also displayed automatically, if received with the ECG snapshot.

When the auto print option is enabled, a hardcopy printout of the rendered ECG snapshot will be sent to a configured local or network printer. The ECG data is printed in the 4×3 layout; analysis results and trend data are also printed, if available.

When the auto sound option is enabled, a user-selectable audio wave file will be played upon receiving an ECG snapshot transmission. The time interval at which the tone is played can also be user-configurable; once, or every 15, 30, or 60 seconds, for example.

When the auto generate PDF option is enabled, the 4×3 layout of the ECG snapshot as well as analysis results and trend data, if available, are rendered as a PDF file. The PDF file generated follows the same naming convention used to assign filenames to incoming ECG snapshot transmissions (FIG. 7), with the exception of the file extension which is appropriately .pdf. The destination server software provides the ability to select the PDF printer/driver used to generate PDF files.

Figure 8:
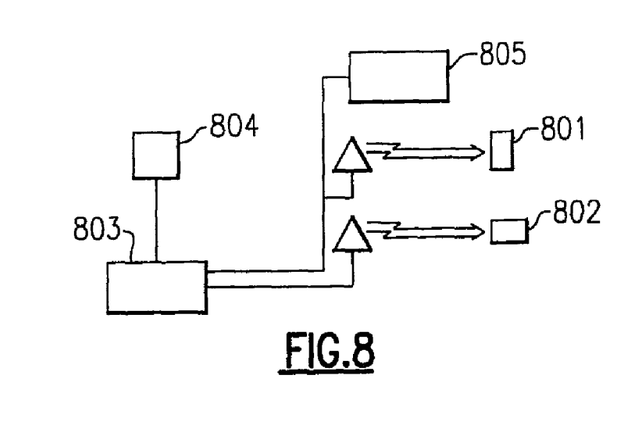
FIG. 8 is a schematic block diagram detailing the user configurable functions of a destination server in accordance with an embodiment of the present invention.

The auto e-mail and auto page options are used to provide notifications to one or more on-call cardiologists that a new ECG snapshot transmission has been received. FIG. 8 is a schematic block diagram detailing the user configurable functions of a destination server in accordance with an embodiment of the present invention. As shown in FIG. 8, an on-call cardiologist carries an internet-enabled handheld PDA 801 and numeric pager 802 to receive notifications of new ECG snapshot transmissions via the destination server 803 (in the embodiment shown, the destination server 803 is a PC which also transmits the rendered data to a printer 804, where it is printed, and to one or more other PC's 805). PDA 801 carried by the cardiologist is preferably a Windows CE or Pocket PC based device and either an externally connected or internally integrated wireless modem providing internet access.

The destination server software preferably allows the configuration of recipient groups used for e-mail forwarding and numeric paging purposes. As previously discussed, when an ECG snapshot transmission is sent from electrocardiogram-performing device 301 to portable transmission device 302, the operator preferably can select a destination location from the destination list on electrocardiogram-performing device 301. The destination location name and IP address are appended to the ECG snapshot record prior to being transmitted from electrocardiogram-performing device 301. When destination server 304 receives an ECG snapshot transmission, the destination name is read from the snapshot data stream. Based on the destination name associated with the ECG snapshot data, destination server 304 can optionally e-mail the generated PDF file as an attachment to one or more recipients, as well as dial one or more numeric pager numbers associated with the given destination name.

Figure 9:
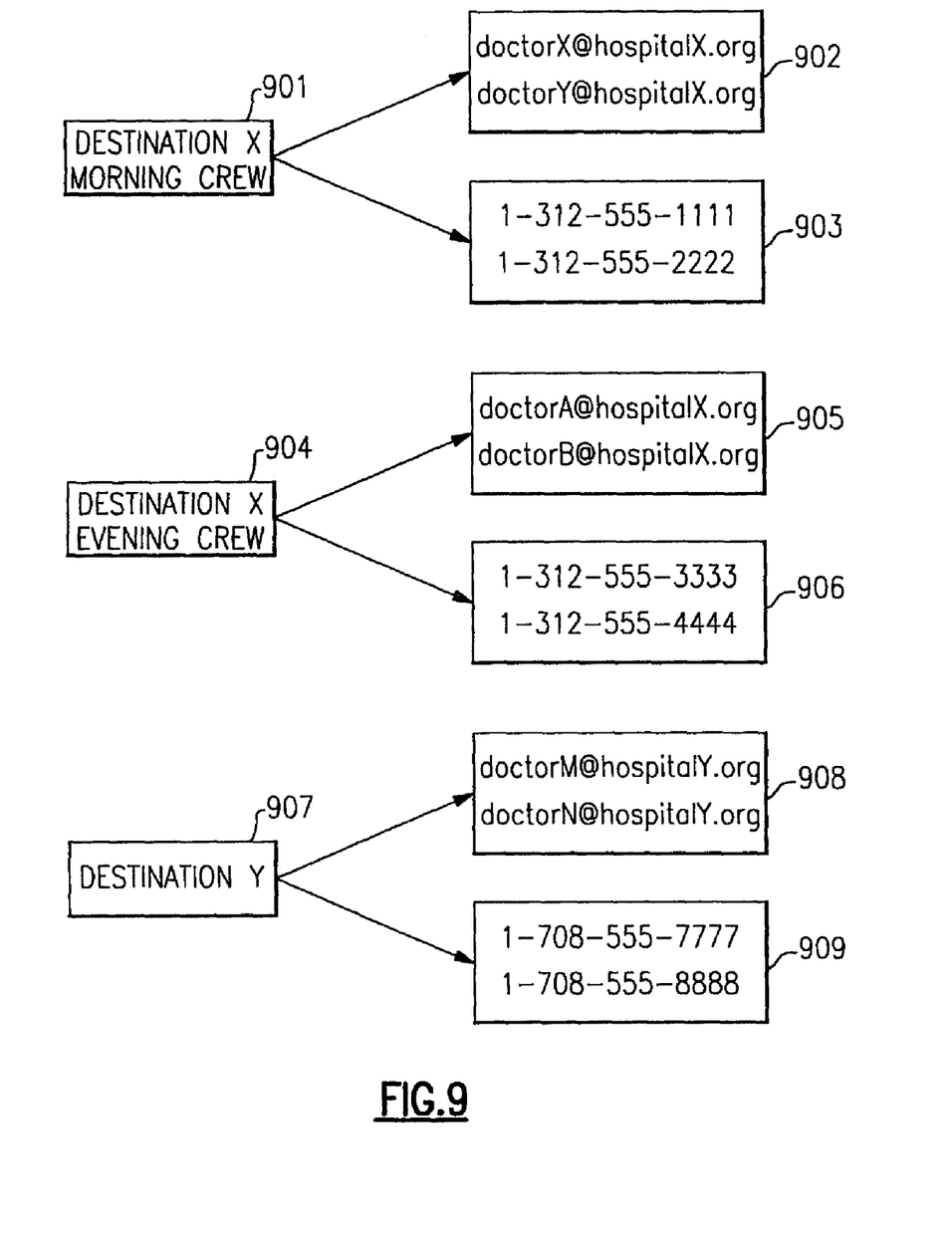
FIG. 9 is a flow diagram showing the relationship between selected destination addresses, and e-mail and notification functions in accordance with an embodiment of the present invention.

The destination server software allows one or more e-mail addresses and one or more numeric pager numbers to be associated with each configured destination location. FIG. 9 is a flow diagram showing the relationship between selected destination addresses, and e-mail and paging functions in accordance with an embodiment of the present invention. FIG. 9 illustrates several examples of the relationship between destination name and e-mail addresses/pager numbers. For example, selecting destination location name Destination X morning crew 901 on electrocardiogram-performing device 301 results in destination server 304 e-mailing files to doctorX@hospitalX.org and doctorY@hospitalX.org in step 902 and dialing pager numbers 1-312-555-1111 and 1-312-555-2222 as shown in step 903. In the same way, selecting destination location name Destination X evening crew 904 on electrocardiogram-performing device 301 results in destination server 304 e-mailing files to doctorA@hospitalX.org and doctorB@hospitalX.org in step 905 and dialing pager numbers 1-312-555-3333 and 1-312-555-444 as shown in step 906. Similarly, selecting destination location name Destination Y 907 on electrocardiogram-performing device 301 results in destination server 304 e-mailing files to doctorM@hospitalY.org and doctorN@hospitalY.org in step 908 and dialing pager numbers 1-312-555-7777 and 1-312-555-8888 as shown in step 909.

Alternatively, destination server 304 can be configured to perform automatic telephone notification in accordance with the destination location name received with the ECG snapshot data. For example, destination server may perform telephone notification to a cardiologist's cellular telephone or regular telephone using a prerecorded message. Additionally, destination server can be configured to perform cellular telephone notification using Short Message Service (SMS) (i.e. text messaging).

As discussed, when destination server 304 receives an ECG snapshot transmission, the destination name is read from the ECG snapshot record. If the destination name contained within the ECG snapshot record matches one of the destinations configured within the destination server's software, automatic PDF e-mailing and/or automatic numeric paging will occur to the respective e-mail addresses and/or pager numbers. If the destination name contained within the ECG snapshot record does not match one of the configured destination names in destination server 304, no e-mail forwarding or numeric paging will occur.

For example, where an on-call cardiologist is carrying a PDA, such PDA may typically be configured to function in low-power (or hibernation mode) operation. The PDA will continue to periodically poll for new e-mail messages on a configurable time interval (from within the e-mail client software) while the PDA continues to operate in standby mode. When a new e-mail message is received, the PDA will typically sound a tone and/or vibrate; the cardiologist can then download the PDF file attachment and use a PDF viewer to examine the newly received PDF file.

The numeric paging process preferably occurs prior to the automated e-mailing process. In the event that the cardiologist's PDA 801 does not support an "always on" mode of operation (i.e., continually connected to the internet even in low-power or standby mode), the numeric page will be received by the cardiologist's on-call pager 802, which alerts him that a new ECG snapshot PDF e-mail attachment is arriving momentarily.

Once the cardiologist has been alerted of a new ECG snapshot via his pager 802 and/or has reviewed the ECG snapshot PDF snapshot attachment, he may call the emergency department directly via his cell phone if he is off site, or he may opt to (or opt not to) assemble the catheterization lab team immediately based on his diagnosis of the ECG snapshot. The actual course of action taken is typically spelled out in the emergency department's accepted operation protocol.

Accordingly, the present invention as described herein provides a method and apparatus for the wireless transmission of data that enables the fast wireless transmission of electronic records. In the field of emergency medicine therefore, the present invention enables the transmission of patient data to qualified emergency medical personnel prior to arrival at an emergency department such that preparations can be made to reduce patient treatment times and increase survival rates.

As mentioned above, the present invention is further directed to a variety of methods including one or more steps corresponding to the description herein.

Any two or more structural parts of the communication systems described herein can be integrated. Any structural part of the communication systems described herein can be provided in two or more parts, which can be held together, if desired or necessary. Similarly, any two or more functions can be conducted simultaneously, and/or any function can be conducted in a series of steps.

The invention claimed is:

1. A communication system, comprising:
means for receiving raw data;
means for acquiring raw data and supplying said raw data to said means for receiving raw data;
means for formatting said raw data to provide formatted data, wherein said means for receiving said raw data further comprises means for selecting at least one destination group from a list comprising more than one destination group;
means for wirelessly transmitting said formatted data;
means for receiving said formatted data, wherein said means for receiving said formatted data further comprises means for creating at least said at least one destination group, wherein each of said at least one destination group comprises at least one means for receiving rendered data;
means for rendering data received by said means for receiving said formatted data to provide rendered data;
at least one means for receiving said rendered data;
means for transmitting said rendered data to each of said at least one means for receiving said rendered data in each of said at least one destination group selected from said list; and
means for automatically notifying a notification device respectively associated with each of said at least one means for receiving said rendered data, wherein a user can select from among at least automatic notification of every transmission of rendered data upon arrival and automatic notification of only transmissions of rendered data for a new patient.

2. A communication system as recited in claim 1, wherein said means for automatically notifying notifies said notification device before transmitting said rendered data to said at least one means for receiving said rendered data.

3. A communication system as recited in claim 1, wherein said means for acquiring raw data is an electrocardiogram-performing apparatus.

4. A communication system as recited in claim 1, further comprising means for generating patient trend data based on said raw data, and wherein said patient trend data is wirelessly transmitted along with said formatted data.

5. A communication system as recited in claim 1, further comprising means for automatically selecting from among a plurality of communication protocols a selected communication protocol according to which said raw data can be formatted to produce formatted data and in which said formatted data can be wirelessly transmitted,
wherein said means for formatting said raw data is a means for formatting said raw data according to said selected communication protocol.

6. A communication system as recited in claim 5, wherein said means for automatically selecting from among a plurality of communication protocol selects said selected communication protocol based on at least one selection criterion selected from the group consisting of:
respective bandwidth detected to be available for each of said communication protocols;
size of said raw data;
identifying communication methods available to said communication system;
detected accuracy of data sent to a receiver and returned from said receiver in any one of said communication protocols;
passage of time without data being received by a receiver; and
detected quantity of dropouts after beginning to attempt to transmit data to a receiving device.

7. A communication system as recited in claim 1, further comprising:
means for communicating to said user at least one parameter selected from the group consisting of:
respective bandwidth detected to be available for each of a plurality of communication protocols, size of said raw data, communication methods available to said communication system, detected accuracy of data sent to a receiver and returned from said receiver in any one of said plurality of communication protocols, passage of time without data being received by a receiver, and detected quantity of dropouts after beginning to attempt to transmit data to a receiving device;

and means for allowing said user to select from among said plurality of communication protocols a selected communication protocol according to which said raw data can be formatted to produce formatted data and in which said formatted data can be wirelessly transmitted.

8. The communication system of claim 1, wherein said at least one means for receiving rendered data comprises personal computers, servers, printers, cellular telephones, pagers and personal digital assistants.

9. The communication system of claim 1, wherein said at least one means for receiving rendered data in said at least one destination group are grouped by said means for transmitting said rendered data to said at least one destination group.

10. The communication system of claim 1, wherein said means for wirelessly transmitting said formatted data is a portable wireless communications device.

11. The communication system of claim 10, wherein said portable wireless communications device comprises a personal digital assistant, a tablet personal computer, a pocket PC-based device or a cell phone.

12. The communication system of claim 1, wherein said means for receiving raw data is a separate means from said means for receiving formatted data.

13. The communication system of claim 1, wherein said means for formatting said raw data is a portable wireless communication device.

14. The communication system of claim 13, wherein said portable wireless communication device comprises a personal digital assistant, a tablet personal computer, a pocket PC-based device or a cell phone.

15. The communication system of claim 1, wherein said means for formatting said raw data is a medical device.

16. A method of communicating data between devices, said method comprising:

acquiring raw data and supplying said raw data to a raw data-receiving device, said raw data-receiving device comprising means for selecting at least one destination group from a list comprising more than one destination group;

formatting said raw data to create formatted data;

wirelessly transmitting said formatted data;

receiving said formatted data in a receiving device, said receiving device comprising means for creating said at least one destination group wherein said at least one destination group comprises at least one rendered data-receiving device;

rendering said formatted data received by said receiving device to create rendered data;

transmitting said rendered data to at least one rendered data-receiving device in said at least one destination group; and automatically notifying a notification device respectively associated with each of said at least one rendered data-receiving device, wherein a user can select from among at least automatic notification of every transmission of rendered data upon arrival and automatic notification of only transmissions of rendered data for a new patient.

17. A method as recited in claim 16, wherein said automatically notifying is carried out before said transmitting said rendered data.

18. A method as recited in claim 16, wherein said raw data is acquired from an electrocardiogram-performing apparatus.

19. A method as recited in claim 16, further comprising generating patient trend data based on said raw data, wherein said patient trend data is wirelessly transmitted along with said formatted data.

20. A method as recited in claim 16, further comprising:

automatically selecting from among a plurality of communication protocols a selected communication protocol, wherein said formatting said raw data is carried out according to said selected communication protocol; and wherein said wirelessly transmitting said formatted data is carried out in said selected communication protocol.

21. A method as recited in claim 20, wherein said method further comprises at least one step selected from the group consisting of:

detecting respective bandwidth available for each of said communication protocols;

detecting a size of said raw data;

identifying communication methods available to said communication system;

detecting accuracy of data sent to a receiver and returned from said receiver in any one of said communication protocols;

detecting passage of time without data being received by a receiver; and detecting quantity of dropouts after beginning to attempt to transmit data to a receiving device.

22. A method as recited in claim 16, further comprising:

detecting at least one parameter selected from the group consisting of:

respective bandwidth detected to be available for each of a plurality of communication protocols, size of said raw data, communication methods available to said communication system, accuracy of data sent to a receiver and returned from said receiver in any one of said plurality of communication protocols, passage of time without data being received by a receiver, and quantity of dropouts after beginning to attempt to transmit data to a receiving device;

communicating to a user said at least one parameter; and selecting from among said plurality of communication protocols a selected communication protocol based on a selection by said user, wherein said formatting said raw data is carried out in said selected communication protocol; and wherein said transmitting said formatted data is carried out in said selected communication protocol.

23. A method as recited in claim 16, wherein said rendering of said formatted data comprises defining line segments which approximate a plurality of data points within said formatted data, instead of identifying each data point which is approximated by said line segment.

* * * * *